United States Patent [19]
Chou et al.

[11] Patent Number: 5,896,198
[45] Date of Patent: Apr. 20, 1999

[54] OPTICAL HETERODYNE-BASED METHOD AND APPARATUS FOR DETERMINING THE CONCENTRATION OF OPTICALLY ACTIVE SUBSTANCES

[76] Inventors: Chien Chou, 5F, No. 37-3, Chuan-Yuan Rd., Pei-Tou Dist., Taipei City; Yeu-Chuen Huang, No. 73-3, Ta-Hua St., Pan-Chiao City, Taipei Hsien; Ching-Mei Feng, No. 7-28, Fu-Yin St., Chian-Chin Dist., Kaohsiung City, all of Taiwan

[21] Appl. No.: 08/967,691

[22] Filed: Nov. 12, 1997

[30] Foreign Application Priority Data

Nov. 11, 1996 [TW] Taiwan ............................ 85113746

[51] Int. Cl.⁶ .................................................. G01B 9/02
[52] U.S. Cl. ...................... 356/349; 356/351; 600/316
[58] Field of Search ............................ 356/346, 349, 356/351, 361; 600/316

[56] References Cited

U.S. PATENT DOCUMENTS

| | | | |
|---|---|---|---|
| 4,523,847 | 6/1985 | Bjorklund et al. ............... | 356/349 |
| 4,750,830 | 6/1988 | Lee . | |
| 4,777,953 | 10/1988 | Ash et al. . | |
| 4,854,322 | 8/1989 | Ash et al. . | |
| 5,009,230 | 4/1991 | Hutchinson ..................... | 600/316 |
| 5,209,231 | 5/1993 | Cote et al. . | |
| 5,341,805 | 8/1994 | Stavridi et al. . | |
| 5,379,764 | 1/1995 | Barnes et al. . | |
| 5,398,681 | 3/1995 | Kupershmidt . | |
| 5,433,197 | 7/1995 | Stark . | |
| 5,448,992 | 9/1995 | Kupershmidt . | |
| 5,477,327 | 12/1995 | Bergman . | |
| 5,533,509 | 7/1996 | Koashi et al. . | |
| 5,535,743 | 7/1996 | Backhaus et al. . | |
| 5,560,356 | 10/1996 | Peyman . | |
| 5,586,133 | 12/1996 | Sommargren . | |
| 5,671,301 | 9/1997 | Kupershmidt . | |
| 5,672,875 | 9/1997 | Block et al. . | |

OTHER PUBLICATIONS

Rabinovitch et al., "Noninvasive Glucose Monitoring of the Aqueous Humor of the Eye: Part I. Measurement of Very Small Optical Rotations," *Diabetes Care*, 5(3):254–258 (1982).

March et al., "Noninvasive Glucose Monitoring of the Aqueous Humor of the Eye: Part II. Animal Studies and the Scleral Lens," *Diabetes Care*, 5(3):259–265 (1982).

Otani et al., "Light Source With Orthogonally Linear Polarized Two–Frequency Beam From Laser Diode and Surface Profile Measurement," *Society of Photo Optical Instrumentation Engineers*, (35)4:1070–1073 (1996).

*Primary Examiner*—Samuel A. Turner
*Attorney, Agent, or Firm*—Christensen O'Connor Johnson & Kindness PLLC

[57] ABSTRACT

In a method for determining concentration of an optically active substance in a medium, a laser beam with two eigen modes of two different temporal frequencies and two orthogonal linear polarized states is generated and passed through the medium. Then, the laser beam that exits the medium is passed through an analyzing polarizer so as to generate an optical heterodyne of the orthogonal linear polarized states. The amplitude of the optical heterodyne from the analyzing polarizer is detected, and the detected amplitude of the optical heterodyne is converted into the concentration of the optically active substance in the medium. An optical heterodyne-based apparatus for performing the above method is also disclosed. The method and apparatus are suitable for noninvasive in vivo glucose, monitoring of the aqueous humor in an eye of an animal.

15 Claims, 4 Drawing Sheets

OPTICAL HETERODYNE-BASED METHOD AND APPARATUS FOR DETERMINING THE CONCENTRATION OF OPTICALLY ACTIVE SUBSTANCES

BACKGROUND OF THE INVENTION

1. Field of the Invention

The invention relates to a method and apparatus for determining the concentration of optically active substances, more particularly to an optical heterodyne-based method and apparatus which is suitable for noninvasive in vivo glucose monitoring of the aqueous humor in an eye of an animal.

2. Description of the Related Art

Optical noninvasive in vivo glucose monitoring using the aqueous humor glucose in an eye of an animal as a measure of the blood glucose concentration is known in the art. Rabinovitch, B., March, W. F., and Adams, R. L., have described an optical glucose monitoring scheme in "Noninvasive Glucose Monitoring of the Aqueous Humor of the Eye: Part I. Measurement of Very Small Optical Rotations", Diabetes Care, Vol. 5, No. 3; pp. 254–258, May–June 1982, and in "Noninvasive Glucose Monitoring of the Aqueous Humor of the Eye: Part II. Animal Studies and the Scleral Lens", Diabetes Care, Vol. 5, No. 3; pp. 259–265, May–June 1982. In the proposed scheme, a polarized incident light beam is modulated by a Faraday day effect modulator before being directed laterally through the anterior chamber of the eye. The light beam through the anterior chamber then passes through a Faraday effect path-length compensator, a crossed analyzing polarizer; and to a light detector. The output of the detector is received by a frequency-selective amplifier, which generates an amplified voltage that is a direct measure of the optical activity of the glucose in the aqueous humor present in the anterior chamber for use in determining the glucose concentration. A feedback mechanism may be included for increased sensitivity.

It is noted that the aforementioned glucose monitoring scheme has a complex construction due to its use of a Faraday affect modulator and path-length compensator, and a feedback mechanism for reducing system instability of the modulator. In addition, noise susceptibility limits the accuracy of the aforementioned scheme.

SUMMARY OF THE INVENTION

The object of the present invention is to provide an optical heterodyne-based method and apparatus which is suitable for noninvasive in vivo glucose monitoring of the aqueous humor in an eye of an animal with high precision, and which has a simple construction.

According to one aspect of the present invention, an optical heterodyne-based apparatus for determining concentration of an optically active substance in a medium, comprises:

generating a laser beam with two eigen modes of two different temporal frequencies and two orthogonal linear polarized states;

passing the laser beam through the medium that contains the optically active substance;

passing the laser beam that exits the medium through an analyzing polarizer so as to generate an optical heterodyne of the orthogonal linear polarized states;

detecting amplitude of the optical heterodyne from the analyzing polarizer; and converting the detected amplitude of the optical heterodyne into the concentration of the optically active substance in the medium.

According to another aspect of the present invention, an optical heterodyne-based apparatus for determining concentration of an optically active substance in a medium, comprises:

a two-frequency laser source for generating a laser beam with two eigen modes of two different temporal frequencies and two orthogonal linear polarized states, the laser beam to be passed through the medium that contains the optically active substance;

an analyzing polarizer, adapted to receive the laser beam that exits the medium, for generating an optical heterodyne of the orthogonal linear polarized states;

an optical heterodyne amplitude detector for receiving the optical heterodyne from the analyzing polarizer and for detecting amplitude of the optical heterodyne; and a computer, connected to the optical heterodyne amplitude detector, for converting the amplitude of the optical heterodyne detected by the amplitude detector into the concentration of the optically active substance in the medium.

BRIEF DESCRIPTION OF THE DRAWINGS

Other features and advantages of the present invention will become apparent in the following detailed description of the preferred embodiments with reference to the accompanying drawings, of which.

DETAILED DESCRIPTION OF THE PREFERRED EMBODIMENTS

Before the present invention is described in greater detail, it should be noted that like elements are denoted by the same references numerals throughout the disclosure.

Figure 1:
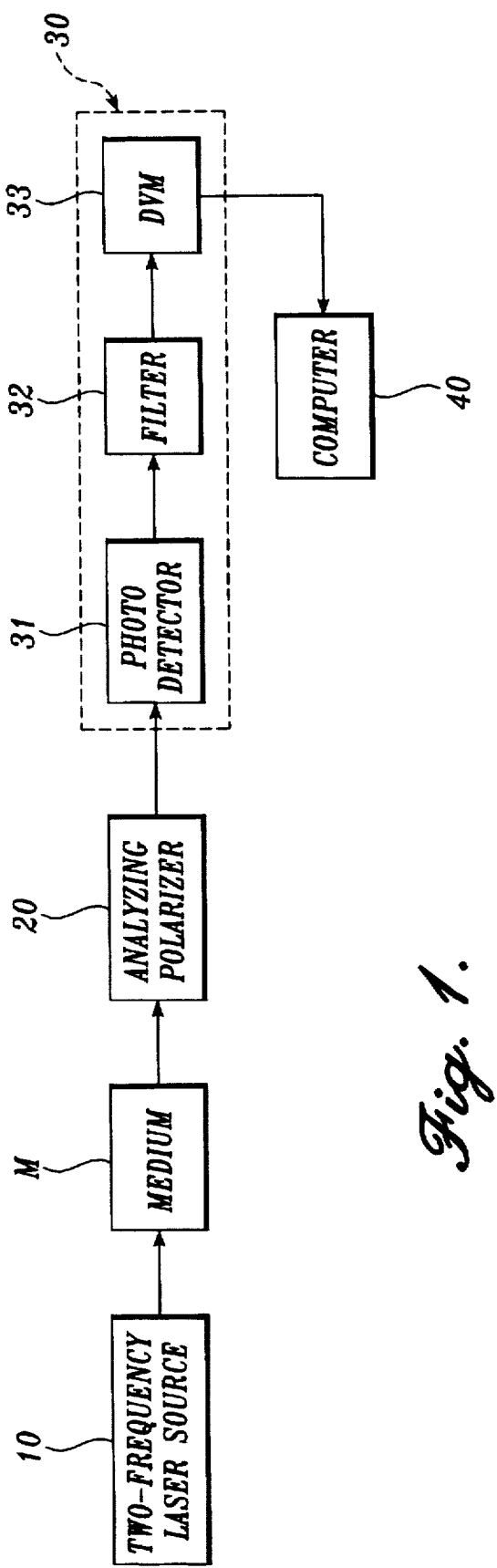
FIG. 1 is a block diagram of the preferred embodiment of an optical heterodyne-based apparatus for determining the concentration of an optically active substance in accordance with the present invention.

Referring to FIG. 1, the preferred embodiment of an optical heterodyne-based apparatus according to the present invention is shown to comprise a two-frequency laser source 10, an analyzing polarizer 20, an optical heterodyne amplitude detector 30 including a photodetector 31, a filter 32 and an amplitude measuring device 33, and a computer 40.

The two-frequency laser source 10 may be a gas or solid state laser, and generates an output laser beam having two eigen modes of two different temporal frequencies, $\omega_0+\omega_1$, $\omega_0+\omega_2$, and two orthogonal linear polarized states that include a P state in the x-axis and an S state in the y-axis. Thus, no beat signal is available from the P and S states of the output laser beam. In this embodiment, the laser source 10 is a Zeeman laser.

The analyzing polarizer 20, such as a linear polarizer, generates an optical heterodyne of the orthogonal linear polarized states. The optical heterodyne amplitude detector 30 detects the amplitude of the optical heterodyne from the analyzing polarizer 20.

When the output laser beam from the laser source 10 is passed through a medium that does not contain an optically active substance before being directed to the analyzing polarizer 20, the output signal of the photodetector 31 of the optical heterodyne amplitude detector 30 can be expressed by:

$$I_r = a_1 a_2 \sin(2\theta) \cos(\Delta\Omega t + \Delta\Phi) \quad (1)$$

which $a_1$, $a_2$ are the amplitudes of the orthogonal linear polarized states of the output laser beam, $\theta$ is the azimuth angle of the analyzing polarizer 20, $\Delta\omega = \omega_1 - \omega_2$, and $\Delta\Phi$ is the difference in the phases of the orthogonal linear polarized states.

When the output laser beam from the laser source 10 is directed through a medium (M) that contains an optically active substance to be measured before passing through the analyzing polarizer 20, the output signal of the photodetector 31 can be expressed by:

$$I_s = a_1 a_2 \sin 2(\theta + \theta_m) \cos(\Delta\omega t + \Delta\Phi) \quad (2)$$

in which $\theta_m$ is the optical rotation angle of the output laser beam exiting the medium (M).

The measurement of the concentration of the optically active substance in the medium (M), in terms of the optical rotation angle of linear polarized light is defined by:

$$[\alpha]_{\lambda,PH}{}^A = \theta_m / CL \quad (3)$$

in which $[\alpha]_{\lambda,PH}{}^A$ is the specific rotation of a molecule of the optically active substance, C is the concentration of the optically active substance in the medium (M), and L is the optical path length of the medium (M).

Therefore, when the temperature (T), wavelength ($\lambda$) pH value of the medium, and the optical path length (L) are constant, a linear relationship between the optical rotation angle ($\theta_m$) and the concentration (C) can be established.

When the concentration of the optically active substance to be measured is very small, the optical rotation angle can be expected to be very small. Under this condition, Equation (2) can be rewritten as $$I_s = 2a_1 a_2 (\theta + \theta_m) \cos(\Delta\omega t + \Delta\Phi) \quad (4)$$

In order to calibrate the apparatus at zero concentration ($\theta_m = 0$), the azimuth angle ($\theta$) is set to 1 degree so that the output amplitude at zero concentration is $2a_1 a_2$. Therefore, the optical rotation angle ($\theta_m$) can be determined as the change in $I_s$ from the zero concentration value divided by the constant $2a_1 a_2$, without any adverse affect due to changes in the index of refraction brought about by differing concentrations of the optically active substance in the medium (M).

Preferably, the analyzing polarizer 20 is a Glan-Thompson polarizer having a high extinction ratio to allow the detection sensitivity of the measuring optical rotation angle to reach $10^{-5}$ degrees.

The output signal of the photodetector 31 is received by the filter 32. The filter 32 is preferably a narrow band pass filter centered at the beat frequency of the temporal frequencies of the output laser beam of the laser source 10 for improved signal-to-noise response. The beat frequency is defined as the difference between the two temporal frequencies. In this embodiment, the amplitude measuring device 33 is a digital voltmeter (DVM) which measures the amplitude of the filtered signal from the filter 32.

The output of the amplitude measuring device 33 is received by the computer 40. The computer 40 can be programmed to make periodic or continuous monitoring of the output of the amplitude measuring device 33, and is responsible for converting the same into the concentration of the optically active substance in the medium (M) through which the output laser beam of the laser source 10 passed.

The optical heterodyne-based apparatus of this invention can be applied in the measurement of the concentration of a solution, such as a glucose solution, in a diffused quartz cell, and to noninvasive in vivo glucose monitoring. In the latter application, the medium is an animal eye, and the output laser beam of the laser source 10 is passed laterally through the anterior chamber of the animal eye. The output laser beam that exits the anterior chamber is optically rotated by the glucose in the aqueous humor present in the anterior chamber by an amount corresponding to the glucose concentration. Therefore, real time noninvasive in vivo glucose monitoring is possible with the use of the apparatus of this invention.

Figure 2:
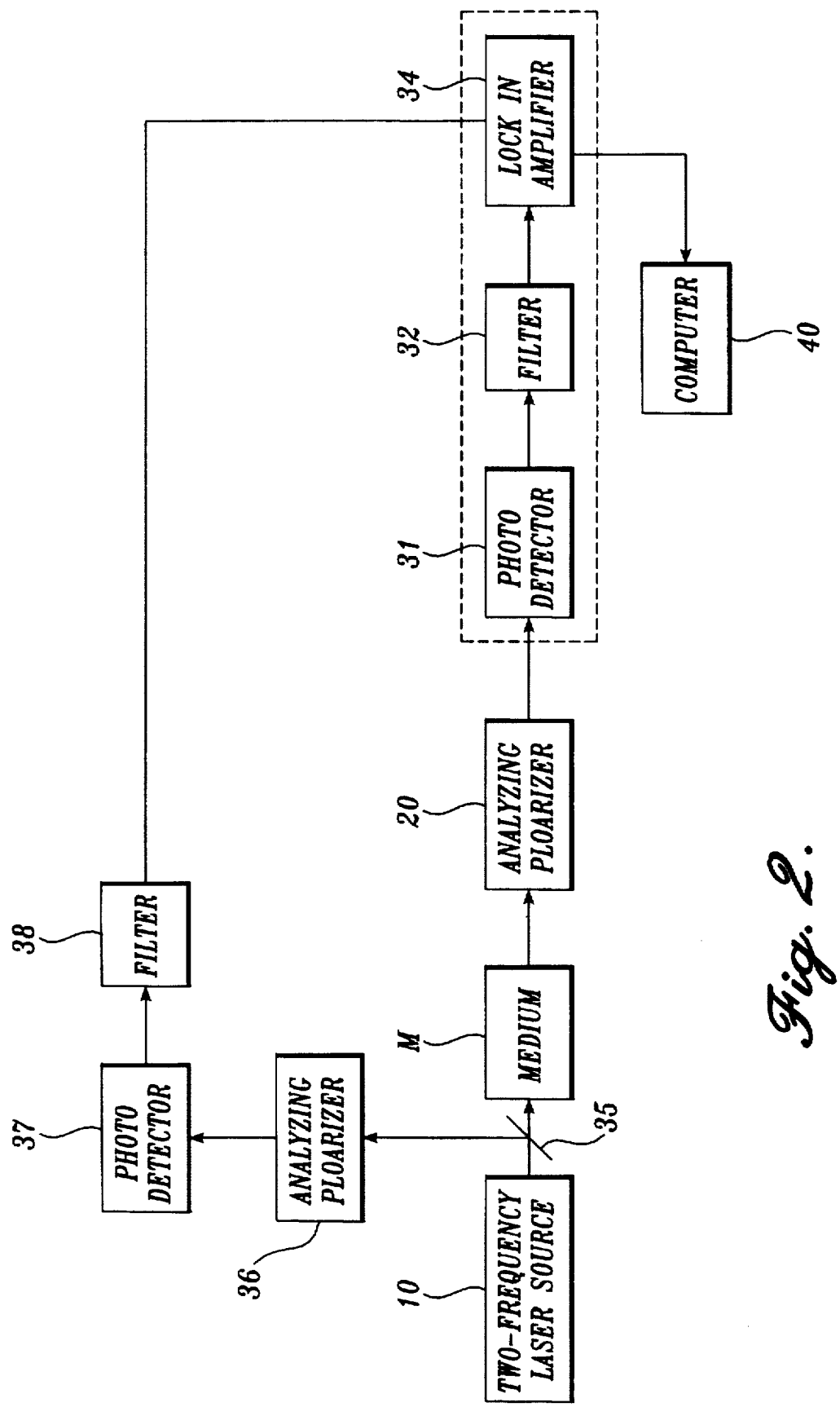
FIG. 2 is a block diagram of another preferred embodiment of an optical heterodyne-based apparatus according to the present invention.

FIG. 2 illustrates another preferred embodiment of an optical heterodyne-based apparatus according to the present invention. The embodiment of FIG. 2 is generally similar to the embodiment described beforehand. However, instead of a digital voltmeter, the amplitude measuring device of this embodiment is a lock in amplifier 34, which is more sensitive than the digital voltmeter. A reference optical signal for the lock-in amplifier 34 is generated by a beam splitter 35, an analyzing polarizer 36, a photodetector 37, and a filter 38. The beam splitter 35 is disposed at the output side of the laser source 10 and splits the output laser beam into a reference beam and a test beam, the latter being passed through the medium (M) that contains the optically active substance to be measured. The reference beam passes through the analyzing polarizer 36, and is detected by the photodetector 37, which generates an output signal corresponding thereto. The output signal from the photodetector 37 is processed by the filter 38 before being supplied to the lock-in amplifier 34.

Figure 3:
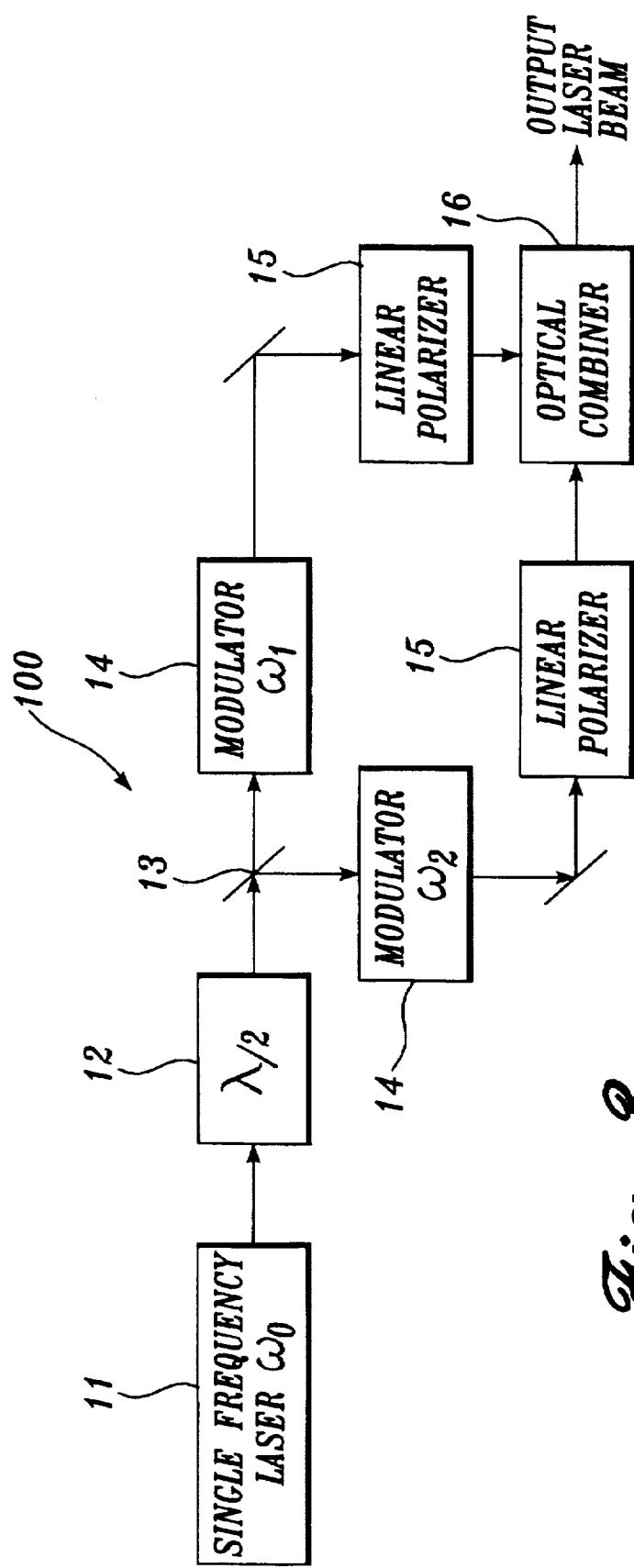
FIG. 3 is a block diagram of a modified two-frequency laser source for the preferred embodiments.

FIG. 3 illustrates a modified embodiment of a two-frequency laser source 100 for the optical heterodyne based apparatus of this invention. As shown, the laser source 100 comprises a stabilized linear polarized single frequency laser 11, a polarized beam splatter 13, a $\lambda/2$ wave plate 12 placed between the single frequency laser 11 and the polarized beams splitter 13, two modulators 14, two linear polarizers 15, and an optical combiner 16.

The single frequency laser 11, which may be a gas or solid state laser, generates an output laser beam that is split into two linear polarized waves by the polarized beam splitter 13. The $\lambda/2$ wave plate 12 is installed to ensure that the intensities of the linear polarized waves are generally the same. The linear polarized waves are received by the two modulators 14, respectively. The modulators 14 may be acousto-optic modulators, electro-optic modulators or any phase modulator, and are used to modulate the linear polarized waves in order obtain two different temporal frequencies. The linear polarizers 15 are orthogonal to each other such that two orthogonal and two different temporal frequency linear polarized waves are generated. Finally, the optical combiner 16 combines the two orthogonal linear polarized waves of two different temporal frequencies to result in a laser output that is similar to that of a Zeeman laser.

If the laser source 100 is applied in the embodiment of FIG. 2, the optical combiner 16 may be replaced by a cube beam splitter to obtain both the reference beam and the test beam.

The two-frequency laser source of the optical heterodyne-based apparatus of this invention should not be limited to those described beforehand. A two-frequency laser source which comprises a laser diode, such as that disclosed by Otani, Y., Tanahashi, A., and Yoshizawa, T. in "Light Source With Orthogonally Linear Polarized Two-Frequency Beam From Laser Diode And Surface Profile Measurement", *Opt. Eng.* 35(4), pp. 1070–1073, April 1996, can also be used in the present invention.

Figure 4:
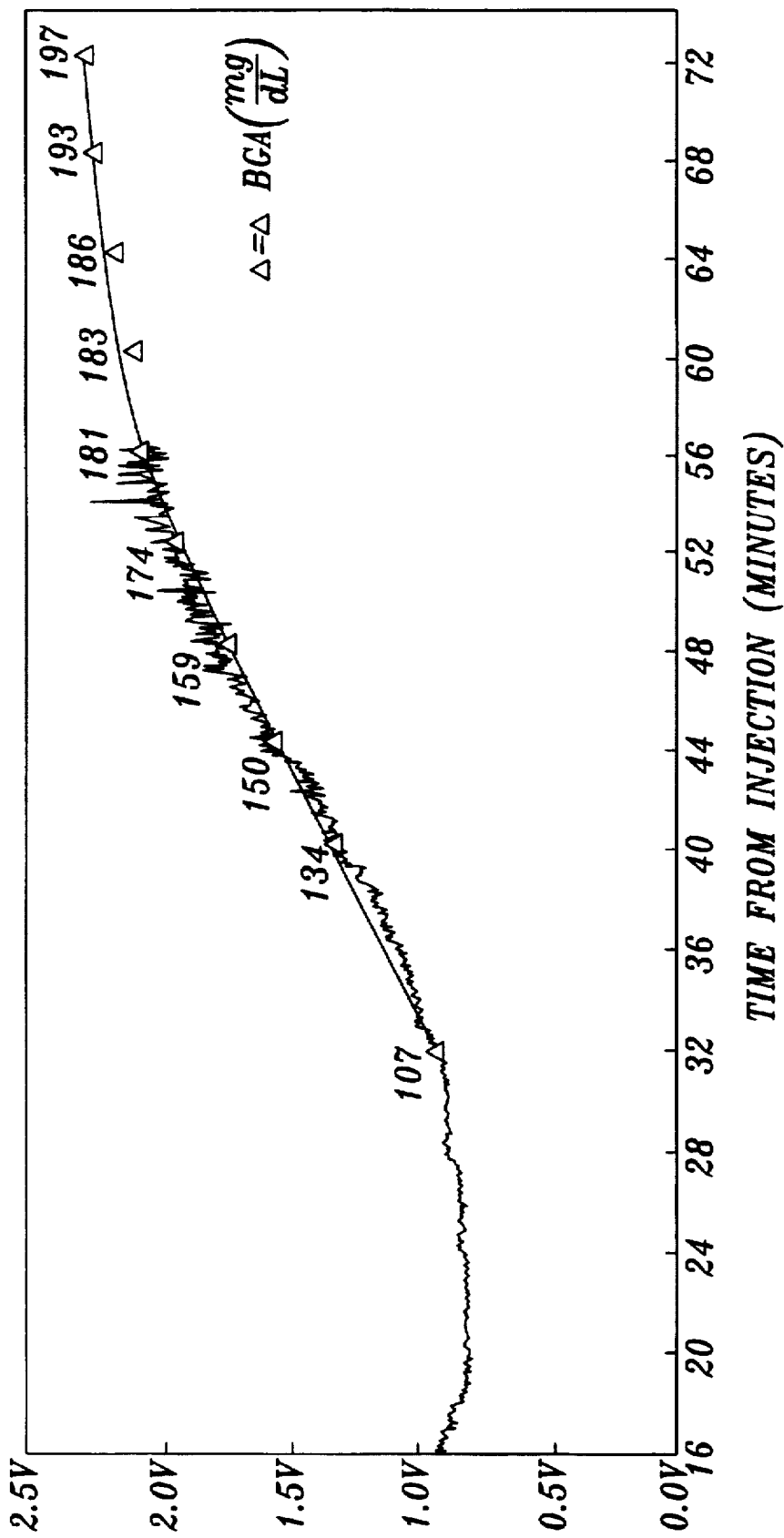
FIG. 4 is a graph of observed test results when the optical heterodyne-based apparatus of this invention is used to measure aqueous humor glucose in comparison with those obtained using the conventional biological glucose assay (BGA) technique.

To verify the precision of the optical heterodyne-based apparatus of this invention, an in vivo test was conducted using a live rabbit. The apparatus was used to monitor continuously and noninvasively the glucose concentration in the aqueous humor present in an eye of the rabbit. At the same time, blood was periodically withdrawn from the rabbit for measurement by the conventional biological glucose assay (BGA) technique. The results, which are shown in FIG. 4, confirm that the precision of the method and apparatus of this invention is comparable to that of the conventional BGA technique.

It has thus been shown that the optical heterodyne-based method and apparatus of the present invention permit noninvasive in vivo glucose monitoring of the aqueous humor in an eye of an animal with high precision and with a simple hardware requirement. The object of the present invention is thus met.

While the present invention has been described in connection with what is considered the most practical and preferred embodiments, it is understood that this invention is not limited to the disclosed embodiments but is intended to cover various arrangements included within the spirit and scope of the broadest interpretation so as to encompass all such modifications and equivalent arrangements.

We claim:

1. An optical heterodyne-based method for determining concentration of an optically active substance in a medium, comprising:

generating a laser beam with two eigan modes of two different temporal frequencies and two orthogonal linear polarized states;

passing the laser beam through the medium that contains the optically active substance;

passing the laser beam that exits the medium through an analyzing polarizer so as to generate an optical heterodyne of the orthogonal linear polarized states;

detecting amplitude of the optical heterodyne from the analyzing polarizer; and converting the detected amplitude of the optical heterodyne into the concentration of the optically active substance in the medium.

2. An optical heterodyne-based apparatus for determining concentration of an optically active substance in a medium, comprising:

a two-frequency laser source for generating a laser beam with two eigen modes of two different temporal frequencies and two orthogonal linear polarized states, the laser beam to be passed through the medium that contains the optically active substance;

an analyzing polarizer, adapted to receive the laser beam that exits the medium, for generating an optical heterodyne of the orthogonal linear polarized states;

an optical heterodyne amplitude detector for receiving the optical heterodyne from the analyzing polarizer and for detecting amplitude of the optical heterodyne; and a computer, connected to the optical heterodyne amplitude detector, for converting the amplitude of the optical heterodyne detected by the amplitude detector into the concentration of the optically active substance in the medium.

3. An optical heterodyne-based method for in vivo noninvasive determination of concentration of an optically active substance in animal, comprising:

generating a laser beam with two eigen modes of two different temporal frequencies and two orthogonal linear polarized states;

passing the laser beam through a portion of the animal having a medium that contains the optically active substance to be measured;

passing the laser beam that exits the medium through an analyzing polarizer so as to generate an optical heterodyne of the orthogonal linear polarized states;

detecting amplitude of the optical heterodyne from the analyzing polarizer; and converting the detected amplitude of the optical heterodyne into the concentration of the optically active substance in the medium.

4. The optical heterodyne-based method as claimed in claim 3, wherein the laser beam is passed through aqueous humor in the anterior chamber of the eye of the animal, and the optically active substance to be measured is glucose.

5. An optical heterodyne-based apparatus for in vivo noninvasive determination of concentration of an optically active substance in an animal, comprising:

a two-frequency laser source for generating a laser beam with two eigen modes of two different temporal frequencies and two orthogonal linear polarized states, the laser beam to be passed through a portion of the animal having a medium that contains the optically active substance to be measured;

an analyzing polarizer, adapted to receive the laser beam that exits the medium, for generating an optical heterodyne of the orthogonal linear polarized states;

an optical heterodyne amplitude detector for receiving the optical heterodyne from the analyzing polarizer and for detecting amplitude of the optical heterodyne; and a computer, connected to the optical heterodyne amplitude detector, for converting the amplitude of the optical heterodyne detected by the amplitude detector into the concentration of the optically active substance in the medium.

6. The optical heterodyne-based apparatus as claimed in claim 5, wherein the laser source comprises a Zeeman laser.

7. The optical heterodyne-based apparatus as claimed in claim 5, wherein the two-frequency laser source comprises:

a stabilized linear polarized single frequency laser;

a polarized beam splitter for splitting output of the single frequency laser into two orthogonal linear polarized waves;

a pair of modulators, each of which modulates a respective one of the linear polarized waves from the polarized beam splitter to obtain two different temporal frequencies;

a pair of linear polarizers that are orthogonal to each other, the linear polarizers being disposed after the polarized beam splitter to obtain orthogonal linear polarized waves; and an optical combiner disposed after the modulators and the linear polarizers to combine the orthogonal linear polarized waves of two different temporal frequencies.

8. The optical heterodyne-based apparatus as claimed in claim 7, wherein the two-frequency laser source further comprises a λ/2 wave plate between the single frequency laser and the polarized beam splitter.

9. The optical heterodyne-based apparatus as claimed in claim 5, wherein the laser source comprises a laser diode.

10. The optical heterodyne-based apparatus as claimed in claim 5, wherein the analyzing polarizer is a linear polarizer.

11. The optical heterodyne-based apparatus as claimed in claim 5, wherein the analyzing polarizer is a Glan-Thompson polarizer.

12. The optical heterodyne-based apparatus as claimed in claim 5, wherein the optical heterodyne amplitude detector comprises:

a photodetector for generating an output signal corresponding to the amplitude of the optical heterodyne received from the analyzing polarizer; and an amplitude measuring device, connected to the photodetector, for measuring amplitude of the output signal of the photodetector.

13. The optical heterodyne-based apparatus as claimed in claim 12, wherein the optical heterodyne amplitude detector further comprises a band pass filter between the photodetector and the amplitude measuring device.

14. The optical heterodyne-based apparatus as claimed in claim 12, wherein the amplitude measuring device comprises a digital voltmeter.

15. The optical heterodyne-based apparatus as claimed in claim 12, wherein the amplitude measuring device comprises a lock-in amplifier.

* * * * *

UNITED STATES PATENT AND TRADEMARK OFFICE
CERTIFICATE OF CORRECTION

PATENT NO. : 5,896,198
DATED : April 20, 1999
INVENTOR(S) : C. Chou et al.

It is certified that error appears in the above-identified patent and that said Letters Patent is hereby corrected as shown below:

COLUMN      LINE

[57]      Abstract      After "glucose" delete ","
1, col. 2      line 14 of text 5      38      "eigan" should read --eigen--
(Claim 1,      line 4)

6      6      "in animal," should read --in an animal,--
(Claim 3,      line 3)

Signed and Sealed this

Ninth Day of November, 1999

Attest:

Q. TODD DICKINSON

*Attesting Officer*      *Acting Commissioner of Patents and Trademarks*

UNITED STATES PATENT AND TRADEMARK OFFICE
CERTIFICATE OF CORRECTION

PATENT NO. : 5,896,198
DATED : Apr. 20, 1999
INVENTOR(S) : Chien Chou, et al

It is certified that error appears in the above-identified patent and that said Letters Patent is hereby corrected as shown below:

On title page, insert item [73] to read as follows:
--[73] Assignee: Chien Chou, Taipei City, Taiwan--

Signed and Sealed this

Eighth Day of August, 2000

*Attest:*

Q. TODD DICKINSON

*Attesting Officer*      *Director of Patents and Trademarks*